United States Patent
Gu et al.

(10) Patent No.: US 7,202,256 B2
(45) Date of Patent: Apr. 10, 2007

(54) PROLINE CCI-779, PRODUCTION OF AND USES THEREFOR, AND TWO-STEP ENZYMATIC SYNTHESIS OF PROLINE CCI-779 AND CCI-779

(75) Inventors: Jianxin Gu, River Edge, NJ (US); Mark E. Ruppen, Garnerville, NY (US); Panolil Raveendranath, Monroe, NY (US); Warren Chew, Outremont (CA); Chia-Cheng Shaw, St. Laurent (CA)

(73) Assignee: Wyeth, Madison, NJ (US)

( * ) Notice: Subject to any disclaimer, the term of this patent is extended or adjusted under 35 U.S.C. 154(b) by 85 days.

(21) Appl. No.: 11/103,779

(22) Filed: Apr. 12, 2005

(65) Prior Publication Data

US 2005/0234086 A1    Oct. 20, 2005

Related U.S. Application Data

(60) Provisional application No. 60/623,594, filed on Oct. 29, 2004, provisional application No. 60/562,069, filed on Apr. 14, 2004.

(51) Int. Cl.
*C07D 498/18* (2006.01)
*C07D 498/22* (2006.01)
*A61K 31/435* (2006.01)
*A61K 31/436* (2006.01)

(52) U.S. Cl. .................. 514/291; 514/411; 540/456; 540/457

(58) Field of Classification Search ........... 540/456, 540/457; 514/291, 411
See application file for complete search history.

(56) References Cited

U.S. PATENT DOCUMENTS

| | | | |
|---|---|---|---|
| 3,929,992 | A | 12/1975 | Sehgal et al. |
| 5,362,718 | A | 11/1994 | Skotnicki et al. |
| 6,277,983 | B1 | 8/2001 | Shaw et al. |
| 2001/0039338 | A1 | 11/2001 | Shaw et al. |
| 2004/0077677 | A1 | 4/2004 | Ashraf et al. |
| 2004/0167152 | A1 | 8/2004 | Rubino et al. |
| 2005/0033046 | A1 | 2/2005 | Chew et al. |

FOREIGN PATENT DOCUMENTS

| | | |
|---|---|---|
| EP | 0589703 A1 | 3/1994 |
| WO | WO 95/28406 A1 | 10/1995 |
| WO | WO 98/54308 A | 12/1998 |
| WO | WO 01/23395 A2 | 4/2001 |
| WO | WO 04/011000 A1 | 2/2004 |
| WO | WO 04/026280 A2 | 4/2004 |
| WO | WO 05/016935 A2 | 2/2005 |

OTHER PUBLICATIONS

Bjorkquist et al, Cyclopolumerization and Regioselective Synthesis of Vinyl Itaconates, J. Org. Chem. 51, pp. 3192-3196, (1986).

*Primary Examiner*—Bruck Kifle
(74) *Attorney, Agent, or Firm*—Howson & Howson LLP; Arnold S. Milowsky

(57) ABSTRACT

Methods for the synthesis of CCI-779 and proline-CCI-779 are described, including a method involving lipase-catalyzed acetylation of 42-hydroxy of rapamycin with a vinyl ester of 2,2-bis(hydroxymethyl) propionic acid in an organic solvent followed by deprotection. Also provided are products containing proline-CCI-779 and uses thereof.

14 Claims, No Drawings

PROLINE CCI-779, PRODUCTION OF AND USES THEREFOR, AND TWO-STEP ENZYMATIC SYNTHESIS OF PROLINE CCI-779 AND CCI-779

CROSS-REFERENCE TO RELATED APPLICATIONS

This application claims the benefit under 35 USC 119(e) of prior U.S. Provisional Patent Application No. 60/623,594, filed Oct. 29, 2004, and prior U.S. Provisional Patent Application No. 60/562,069, filed Apr. 14, 2004.

BACKGROUND OF THE INVENTION

Rapamycin 42-ester with 2,2-bis(hydroxymethyl) propionic acid (CCI-779) is an ester derivative of rapamycin which has demonstrated significant inhibitory effects on tumor growth in both in vitro and in vivo models. The preparation and use of hydroxyesters of rapamycin, including CCI-779, have been described in U.S. Pat. Nos.: 5,362,718 and 6,277,983.

Esterification of rapamycin at the 42-position was previously conducted by directly reacting rapamycin with acylating agents. However, as rapamycin contains two secondary hydroxyl groups at positions 31 and 42, attempts to discriminate between these two functional centers in order to achieve a selective synthesis of 42-monoacylated product still posed a difficult challenge. Currently, a regioselective process for the preparation of CCI-779 involves at least five steps (U.S. Pat. No. 6,277,983, International Patent Publication No. WO 01/23395). First, rapamycin is treated with a silylation agent to form rapamycin 31,42-bis-silyl ether, and then the 42-silyl ether protection group is selectively removed to provide rapamycin 42-OH-31-silyl ether. This freed 42-OH was then acylated with 2,4,6-trichlorobenzyl mixed anhydride of 2,2,5-trimethyl[1,3-dioxane]-5-carboxylic acid and two subsequent deprotection steps furnish the desired CCI-779.

CCI-779 binds to and forms a complex with the cytoplasmic protein FKBP, which inhibits an enzyme, mTOR (mammalian target of rapamycin, also known as FKBP12-rapamycin associated protein [FRAP]). Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from G1 to S. CCI-779 has been demonstrated to be effective in multiple applications, including inhibition of central nervous system cancer, leukemia, breast cancer, prostate cancer, melanoma, gliomas, and glioblastoma.

What are needed are more efficient methods for regiospecific production of CCI-779, and analogs thereof.

SUMMARY OF THE INVENTION

The present invention provides a proline analog of CCI-779 (proline-rapamycin 42-ester with 2,2-bis(hydroxymethyl)propionic acid or proline-CCI-779) and methods of synthesizing same. Proline-CCI-779 is an active drug substance useful in oncology and other associated indications (immunosuppression, anti-inflammatory, anti-proliferation and anti-tumor).

In one aspect, the synthesis of proline-CCI-779 is accomplished through bis-silylation of proline rapamycin, mono-de-protecting 31,42-bis-trimethylsilyl proline rapamycin, and acylating the mono-silyl proline rapamycin followed by hydrolysis.

In another aspect, the invention provides a two-step enzymatic process involving a regiospecific acylation of rapamycin, using a microbial lipase and an activated ester derivative of 2,2-bis(hydroxymethyl)propionic acid in an organic solvent, followed by deprotection to give CCI-779.

In another aspect, the method of the invention permits synthesis of proline CCI-779 from proline-rapamycin, a closely related compound of rapamycin within the rapamycin family.

Other aspects and advantages of the invention will be readily apparent to one of skill in the art.

DETAILED DESCRIPTION OF THE INVENTION

This invention describes a proline analog of rapamycin dihydroxyesters and uses thereof. In one embodiment, the invention provides a proline CCI-779, which is characterized by the core structure:

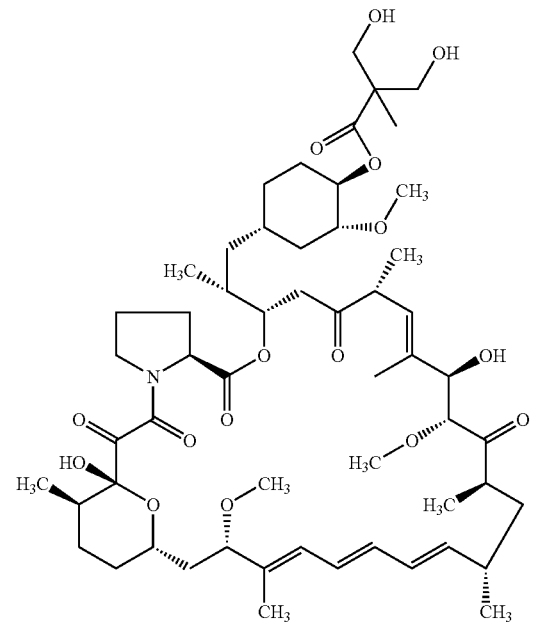

Proline-CCI-779

The invention further provides a method of synthesizing the proline analog of rapamycin dihydroxyesters. In one embodiment, a proline rapamycin is used as a starting material. Rapamycin and its preparation are described in U.S. Pat. No. 3,929,992, issued Dec. 30, 1975. Alternatively, rapamycin may be purchased commercially [Rapamune®, Wyeth]. Proline rapamycin and its preparation have been described. See, e.g., European Patent No. 0589703.

In one embodiment, proline rapamycin is bis-silylated to form 31,42-bis-trimethylsilyl proline rapamycin. Silylating agents that can be used for this transformation include, e.g., commercially available chloroalkylsilanes, such as chlorotrimethylsilane, chlorotriethylsilane, chlorotripropylsilane or chlorotriisopropylsilane. In one embodiment, the silylating agent is chlorotrimethylsilane. Although bulkier silylating agents can be used, such agents require more time to deprotect in acidic media in subsequent reactions. Furthermore, the longer the reaction time in acidic media, the more degradation by-products are formed. In another embodiment, the silylating reaction is performed with trimethylsilyl chloride with a suitable organic base and a suitable organic solvent at cold temperatures to form 31,42-bis-trimethylsilyl proline rapamycin. In one embodiment, the reaction temperature is about 0 to 5° C. In other embodiments, the reaction is conducted at lower temperatures, resulting in a longer reaction time. Suitable organic solvents including, e.g., DMF, can be readily selected. In one embodiment, ethyl acetate is the solvent. Similarly, suitable organic bases can be readily selected from among those known in the art, e.g., imidazole, 1-methyl imidazole, trialkylamines and N,N-diisopropylethylamine. In one embodiment, the base is imidazole, resulting in a completed reaction in less than 1 hour, under the conditions described herein.

Mono-deprotection at the 42-position at 0 to 5° C. under dilute acid conditions provides 31-trimethylsilyl proline rapamycin.

Acylation of mono-silyl proline rapamycin is achieved using 2,4,6-trichlorobenzyl mixed anhydride of 2,2,5-trimethyl[1,3-dioxane]-5-carboxylic acid in the presence of 4-dimethylaminopyridine or a similar catalyst in methylene chloride at −15 to −10° C. to give an intermediate. In another embodiment, mono-silyl proline rapamycin is coupled with the acid chloride of 2,2,5-trimethyl[1,3-dioxane]-5-carboxylic acid in the presence of an organic base catalyst such as 4-dimethylaminopyridine. Other organic catalysts can be substituted for 4-dimethylaminopyridine, including, e.g., other tertiary organic bases such as N,N-dimethylaniline, pyridine, triethylamine, and diisopropylethylamine, among others.

In one embodiment, the solvent for the acylation reaction is methylene chloride. In other embodiments, THF, diethyl-ether or t-butyl methyl ether is used. The reaction can be performed at temperatures less than 0° C. In one embodiment, the reaction is performed at −10° C., or lower. In one embodiment, mono-silyl proline rapamycin is coupled with a mixed anhydride and dimethylaminopyridine in methylene chloride at −12° C. to give an intermediate product.

In another embodiment, acylation may be performed as described in US Patent Application Publication No. US 2005/0033046 A1 (published Feb. 10, 2005). Accordingly, in one embodiment, acylation of mono-silyl proline rapamycin is achieved using 2,4,6-trichlorobenzyl mixed anhydride of a phenylborinane in the presence of 4-dimethylaminopyridine or a similar catalyst in methylene chloride at −11 to −5° C. to give an intermediate. In another embodiment, the phenylborinane is 2-phenyl-1,3,2-dioxoborinane-5-carboxylic acid. In yet another embodiment, the phenylborinane is a 2-phenyl-1,3,2-dioxaborinan-4-yl, wherein the phenyl is optionally substituted. In still another embodiment, the phenylborinane is 5-methyl-2-phenyl-1,3,2-dioxaborinane-5-carboxylic acid.

In a further embodiment, the phenyl group is substituted with an alkyl, such as a $C_1$, $C_2$, $C_3$, $C_4$, $C_5$, or $C_6$ alkyl. Other aryl-(including phenyl-)boronic acids may be used in this reaction. These include mono, di, and tri-substituted arylboronic acids in which the substituents are the same or different. Substituents on the aryl group include halogen, alkyl, alkoxy, aryloxy (e.g., phenoxy), aralkyl, nitro, cyano, and fused phenyl such as napthalylboronic acid. The term alkyl when used as a group or part of a group such as alkoxy or aralkyl includes -alkyl moieties of 1 to 12 carbon atoms, e.g., 1–6 carbon atoms. The term aryl as a group or part of a group, e.g., aralkyl or aryloxy, means an aromatic group including those of 6–10 carbon atoms, e.g., phenyl or napthyl.

In one embodiment, the solvent for the acylation reaction is methylene chloride. In other embodiments, THF, diethyl-ether or t-butyl methyl ether is used. The reaction can be performed at temperatures less than 0° C. In one embodiment, the reaction is performed at −10° C., or lower. In one embodiment, mono-silyl proline rapamycin is coupled with a mixed anhydride and dimethylaminopyridine in methylene chloride at −12° C. to give intermediate product.

Mild acidic hydrolysis in a suitable solvent (e.g. THF) and temperature provides the proline analog of CCI-779. In one embodiment, a dilute inorganic acid such as sulfuric, hydrochloric or phosphoric acid is used. In another embodiment, dilute aqueous sulfuric acid is used. The concentrations range from 0.1 N to about 3 N. In one embodiment, the concentration is 2 N, as under these conditions both the acetal and silyl protecting groups are hydrolyzed at the same time. Under more dilute acidic conditions, hydrolysis takes longer to complete. In one embodiment, this step is carried out at 25° C. or below, or about 0 to 5° C.

Purification can be accomplished by methods known to those of skill in the art including, e.g., chromatography followed by a final crystallization (e.g., by ether treatment) to furnish a purified proline CCI-779.

In another embodiment, this invention provides a novel process for the preparation of rapamycin 42-ester with 2,2-bis(hydroxymethyl)propionic acid (CCI-779) and proline-CCI-779. The process is described below for the preparation of CCI-779. However, proline-CCI-779 may be prepared by the same process from proline rapamycin, as described below.

The synthesis requires two steps. The first step is a microbial lipase-catalyzed acylation of rapamycin with an activated ester of 2,2-bis(hydroxymethyl)propionic acid derivative in an organic solvent. This reaction is highly regioselective, resulting in the exclusive formation of mono-42-acylated product (i.e., protected CCI-779), in nearly quantitative yield. Subsequent deprotection furnishes CCI-779 in excellent overall yield. Compared with chemical preparation, this chemo-enzymatic route offers a much shorter procedure with higher yield. Further, this method does not require any steps to protect the rapamycin's 31-OH group.

The following scheme illustrates this enzymatic preparation of CCI-779. The examples that follow are intended to exemplify the claimed invention, and should not be construed as limiting the disclosure or the claimed invention. Rapamycin and its preparation are described in U.S. Pat. No. 3,929,992, issued Dec. 30, 1975. Alternatively, rapamycin may be purchased commercially [Rapamune®, Wyeth].

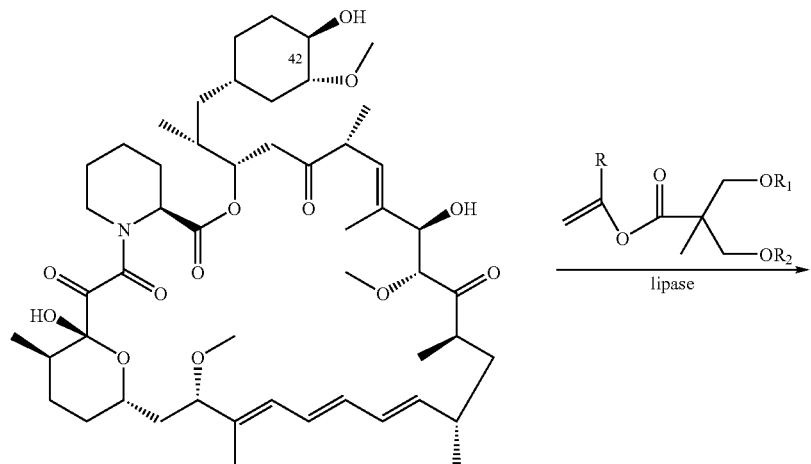
rapamycin
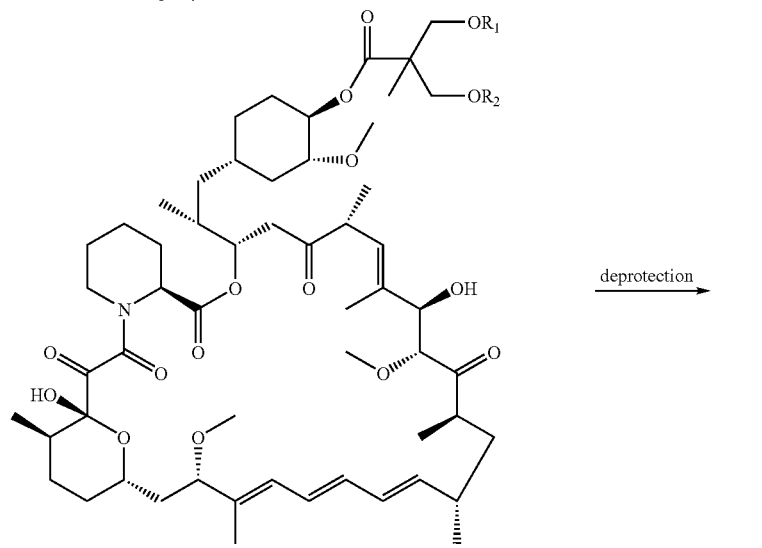
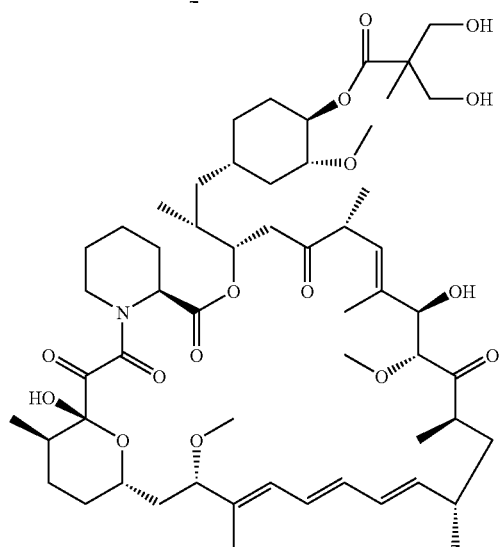
CCI-779

Identification of a suitable activated ester of 2,2-bis(hydroxymethyl) propionic acid side chain has been found to be the key to the success of this lipase-catalyzed acylation. The inventors have found that the corresponding enol esters provide the highest activity and the best yield, especially the vinyl ester. However, other acylation reagents such as methyl, ethyl esters, 2,2,2-trichloroethyl, 2,2,2-trifluoroethyl esters and N-succinimidyl ester may also be used. The protecting group at propionic acid's two bis-hydroxyl groups also plays an important role in the reaction. In one embodiment, cyclic ketals and cyclic boronates are used. However, other protecting groups can be selected from among protecting groups small enough to accommodate this side chain into the enzyme's active site.

The activated ester of 2,2-bis(hydroxymethyl) propionic acid has the structure of formula below

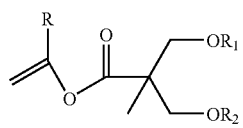

wherein R is hydrogen or methyl, $R_1$ and $R_2$ are hydrogen, or together form a ketal with the structure,

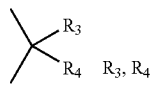

are each, independently, hydrogen, $C_{1-6}$ alkyl, either linear or branched, or together form $C_{5-7}$ cycloalkyl or together form a cyclic boronate with the structure,

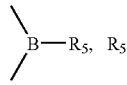

is selected from methyl, ethyl, n-propyl, iso-propyl, n-butyl, iso-butyl and phenyl. Vinyl ester (R=H) with isopropylidene ketal (I) or methyl boronate (II) protecting group has been selected to illustrate the process of this invention.

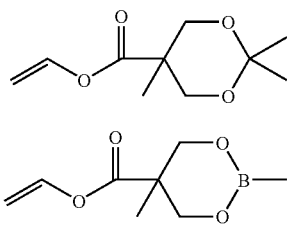

In one embodiment, the first step of process of invention is performed by reacting rapamycin with a vinyl ester (I) or (II) in the presence of a lipase of microbial origin in a suitable organic solvent under optimal temperature for a certain period of time.

As used herein, "microbial lipases", i.e., lipases with microbial origin, include enzymes which were originally isolated from a non-eukaryotic source, such as, *Aspergillus niger, Candida antarctica, Candida rugosa, Mucor miehei, Pseudomonas cepacia, Pseudomonas fluorescens, Rhizopus delemar*. However, the enzyme selected for use in the invention need not be directly isolated and purified from the original source, but can be prepared synthetically or recombinantly, or through other suitable means. A variety of these enzymes are available from some commercial sources. Further, these enzyme preparations can be used as crude, partially purified, purified or immobilized from different microbial origin under different trade names by various suppliers.

In one embodiment, lipase PS-C "Amano" II, an immobilized form of lipase PS from Amano, is used in the method of the invention. However, other lipases can be selected for use in the invention. Such lipases provide a degree of conversion of rapamycin to protected CCI-779 intermediate of greater than 60%, greater than 75%, or greater than 90%. In a further embodiment, such lipases avoid the formation of a significant amount of seco derivative resulting from lipase-catalyzed hydrolysis.

The lipase is used in an effective catalytic amount, i.e., an amount which effectively catalyzes, at a reasonable rate of reaction, the acylation of 42-hydroxyl of rapamycin to form the protected CCI-779. Those skilled in the art will appreciate that the enzyme can be used in amounts of about 25 to about 300 wt % (relative to the amount of rapamycin). In one embodiment, the enzyme is used in amounts of about 50 to about 250 wt %, about 50 to about 200 wt %, or about 75 to about 150 wt %.

Suitable organic solvents include, but are not limited to, toluene, tert-butyl methyl ether (TBME), ethyl ether, THF (tetrahydrofuran), MeCN, $CH_2Cl_2$, $CHCl_3$, $^iPr_2O$, hexane, dioxane, or mixtures including these solvents. In one embodiment, TBME (tert-butyl methyl ether) is used. It will be appreciated by those skilled in the art that the solvent is used in an amount which can effectively dissolve all or part of starting rapamycin at the beginning and allows the reaction to proceed at a reasonable rate. For example, a solvent, such as TBME, can be used in an amount of at least 4 wt volume (i.e, a volume that is in an excess of 4 times (4×) the amount of rapamycin) to about 10 wt volume, or about 5 to 8 wt volume.

TBME may contain residual water (e.g., about 0.05%) which could decompose the rapamycin into a so-called, seco-derivative, a macro lactone-ring opened product. In order to minimize this side-reaction, a low amount of moisture is maintained in the reaction system. In one embodiment, an anhydrous solvent is used with a standard commercial preparation of the lipase catalyst. In another embodiment, moisture can be controlled through adjusting the amount of water present in the lipase solution by adding a drying agent. In yet another embodiment, a molecular sieve can be used to control the moisture. Since a molecular sieve will slow the reaction down, more enzyme can be added to compensate, or a longer reaction time can be used. Where a molecular sieve is used, a 5 Å sieve is particularly desirable. However, other sieve sizes, including, 4 Å and 3 Å, among others, can be readily utilized. Suitable molecular sieves are available from a variety of commercial sources. In still another embodiment, drying agents such as $MgSO_4$, $Na_2SO_4$, among others, can be used to control the moisture content.

The reaction is conducted at a temperature low enough to reduce the formation of unwanted by-product, but not so low as to require an unreasonably long reaction time. A suitable temperature for this enzymatic process can be in the range of about 20° C. to about 75° C., about 30° C. to 65° C., or about 40° C. to 55° C. In one embodiment, the temperature for the reaction is permitted to proceed at 45° C. when TBME is used as solvent. Under such conditions, the reaction can proceed virtually to completion (>99% conversion) within 48 hours. However, lower or higher temperatures can be used, and the length of time for reaction varied, as described herein. In another embodiment, the reaction may be permitted to proceed for about 12 hours to 120 hours, 18 hours to 96 hours, 24 hours to 72 hours, or about 30 hours to 60 hours, as desired or needed. The length of time of the reaction is not a limitation on the present invention. In a further embodiment, the reaction is performed under $N_2$ until all starting material is consumed. The reaction can be monitored by various techniques such as thin layer chromatography (TLC) and high performance liquid chromatography (HPLC). Alternatively, other monitoring methods can be used by one of skill in the art.

In one embodiment, by mixing rapamycin, 100 wt % (relative to the amount of rapamycin) lipase PS-C "Amano" II and isopropylidene ketal protected vinyl ester of 2,2-bis (hydroxymethyl)propionic acid (I) in anhydrous TBME at 45° C. for 48 hours, after removing enzyme by filtration, ketal protected CCI-779 was obtained in >98% yield.

In another embodiment, the process is conducted by mixing rapamycin, 160 wt % lipase PS-C "Amano" II and methyl boronate protected vinyl ester of 2,2-bis(hydroxymethyl)propionic acid (II) in anhydrous tert-butyl methyl ether (TBME) at 45° C. for 60 hours, after removing enzyme by filtration, cyclic methyl boronate protected CCI-779 was obtained in high yield based on the recovered rapamycin.

Following the enzymatic installation of either ketal- or boronate-protected 2,2-bis(hydroxymethyl)propionic acid into the 42-position of rapamycin, CCI-779 can be obtained by subsequent de-protection of the resulting intermediate.

In the case of the boronate derivative, removal of boronate protecting group can be realized by using an alcoholic solvent. In this embodiment of the invention, a suitable alcoholic solvent can be readily selected from the group consisting of methanol (MeOH), ethanol, propanol, isopropanol, butanol, iso-butanol, ethylene glycol, 1,3-propanediol and 2-methylpentane-2,5-diol, or a mixture of these solvents. In one embodiment, the crude product resulting from the enzyme reaction is dissolved in MeOH and the boronate moiety in CCI-779 forms the volatile dimethyl boronate by exchange with MeOH is then evaporated along with solvent under reduced pressure. The remaining residue contains desired CCI-779 along with some unreacted rapamycin, which can be separated by general methods such as silica gel chromatography.

The removal of the ketal protecting group can be accomplished under mildly acidic conditions. In general, the procedure published in U.S. Pat. No. 6,277,983 and documents cited therein can be followed. In one embodiment, the deprotection is carried out in a single phase aqueous acid/organic solvent system, e.g., diluted sulfuric acid in tetrahydrofuran (THF), such as 2 N $H_2SO_4$/THF at about 0 to 5° C. However, this reaction can take about 3 days or more to complete and solvent extraction is needed to recover the product from aqueous media after reaction is complete.

In another embodiment, this acid promoted deprotection can be performed in other water miscible solvents such as acetonitrile (MeCN), n-propanol and iso-propanol. These solvents can be used either alone or as a mixture between acetonitrile and n-propanol or iso-propanol. The ratio of mixed solvent can be varied as described herein, from about 5 parts of acetonitrile with 1 part of propanol (v/v), to about 1 part of acetonitrile with 5 parts of propanol. This ratio is not the limitation of the present invention. When the above solvents or their mixtures are used as reaction medium, in one embodiment aqueous sulfuric acid is used, as it minimizes the formation of impurities generated when other acids, such as aqueous hydrochloric acid, are employed, as described in U.S. Pat. No. 5,362,718. The concentration of aqueous sulfuric acid can be in the range of 3 N to 0.25 N, about 2 N to 0.35 N, or about 1.5 N to 0.5 N. The reaction may be carried out at a temperature about 25° C. or below, about −5° C. to about 10° C., or about 0° C. to about 5° C. When the reaction is complete, the crude product can be recovered by solvent extraction as described in U.S. Pat. No. 6,277,983 (International Patent Publication No. WO 01/23395), or via precipitation by adding the reaction mixture to an ice-cold (0° C. to 5° C.) phosphate buffer. In one embodiment, the concentration of phosphate buffer is in the range of about 2 M to 0.05 M, 1 M to 0.1 M, or 0.5 M to 0.15 M, with a pH value in the range of 6 to 9, or 7.5 to 8.5. In one embodiment, the deprotection is carried out in n-propanol with 1.2 N $H_2SO_4$ at 0° C. to 5° C. and the reaction is completed within 24 h, the crude is then recovered as a off-white powder by adding reaction mixture to phosphate buffer (0.5 M, pH 8) cooled with an ice-water bath. In another embodiment, the deprotection is carried out in a mixed solvent of MeCN-n-propanol (2.5/1.5 v/v) at 0° C. to 5° C., the reaction was done in 28 hours in the presence of 0.6 N $H_2SO_4$, and the product is recovered as an off-white powder by adding reaction mixture to phosphate buffer (0.25 M, pH 7.8)

In another embodiment, CCI-779 could be obtained by direct hydrolysis of enzymatic reaction mixture using aqueous 2 N $H_2SO_4$ in THF without the isolation of crude ketal-protected CCI-779. In this process, the enzymatic reaction is carried out as described above. When reaction is complete, the enzyme is filtered off and washed with 2 volumes of THF, the mixture is then concentrated to a certain volume and diluted with THF. Following treatment with 2N $H_2SO_4$ at 0–5° C. for a certain period of time, CCI-779 can be isolated in high yield.

The synthetic route of the invention provides several distinct advantages over the synthetic methodology published in U.S. Pat. Nos. 5,362,718 and 6,277,983. These advantages include ease of processing, with only two-step manipulation involved, and improved overall yields of the desired 42-ester. For example, the synthetic methodology described in U.S. Pat. No. 5,362,718 provides the isopropylidene ketal-protected CCI-779 in a 35% yield, and the synthetic methodology described in U.S. Pat. No. 6,277,983 provides 85% yield, whereas the two-step enzymatic process described herein furnishes the product in nearly quantitative yield.

In another embodiment, this provides a process for preparing proline-CCI-779, a closely related compound to CCI-779, from proline-rapamycin by the same enzymatic process described herein. Proline-rapamycin, a minor component from rapamycin fermentation crude, is only structurally different from an amino acid unit, i.e., instead of pipecolinic acid in rapamycin, it is replaced by proline. Proline rapamycin, proline-CCI-779 and its derivatives are described in EP 589703.

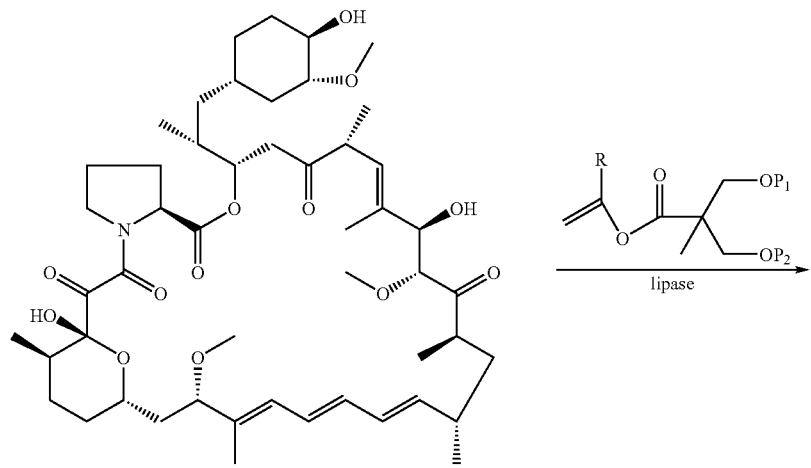
proline-rapamycin
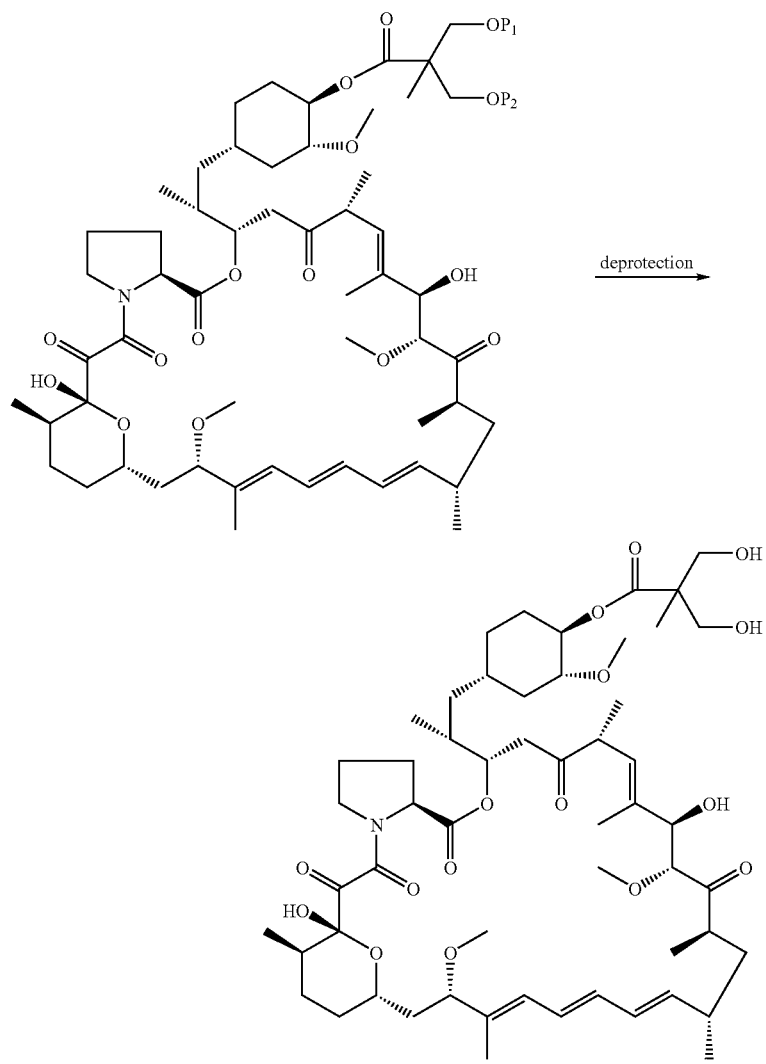
Proline-CCI-779

The resulting CCI-779 and proline CCI-779 prepared according to this invention is useful in pharmaceutical compositions. Such compositions can be formulated by any suitable method described in the art for rapamycin or derivatives thereof.

Oral formulations containing the active compounds as described herein may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. In one embodiment, surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In one embodiment, oral formulations for rapamycin 42-ester with 3-hydroxy-2-(hydroxymethyl)-2-methylpropionic acid are described in US Published Patent Application No. US 2004-0077677 A1 (also U.S. patent application Ser. No. 10/663,506), which are hereby incorporated by reference. Such an oral formulation contains a granulation prepared using a wet granulation process. Similar oral formulations can be prepared using the proline-CCI-779 of the invention.

In some cases it may be desirable to administer the compounds directly to the airways in the form of an aerosol.

The compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

In one embodiment, injectable formulations are described in U.S. Patent Publication No. US 2004-0167152 A1 (also U.S. patent application Ser. No. 10/626,943), which are hereby incorporated by reference. Similar parenteral formulations for proline-CCI-779 may be readily prepared.

In another embodiment, the injectable formulation useful in the invention provides a CCI-779 or a proline-CCI-779 cosolvent concentrate containing a parenterally acceptable solvent and an antioxidant as described above and a parenteral formulation containing a CCI-779 or a proline-CCI-779, composed of a CCI-779 or a proline-CCI-779, a parenterally acceptable cosolvent, an antioxidant, a diluent solvent, and a surfactant. Any given formulation useful in this invention may contain multiple ingredients of each class of component. In one embodiment, a parenterally acceptable solvent can include a non-alcoholic solvent, an alcoholic solvent, or mixtures thereof. Examples of suitable non-alcoholic solvents include, e.g., dimethylacetamide, dimethylsulfoxide or acetonitrile, or mixtures thereof. "An alcoholic solvent," may contain one or more alcohols as the alcoholic solvent component of the formulation. Examples of solvents useful in the formulations invention include, without limitation, ethanol, propylene glycol, polyethylene glycol 300, polyethylene glycol 400, polyethylene glycol 600, polyethylene glycol 1000, or mixtures thereof. These cosolvents are particularly desirable because degradation via oxidation and lactone cleavage occurs to a lower extent for these cosolvents. Further, ethanol and propylene glycol can be combined to produce a less flammable product, but larger amounts of ethanol in the mixture generally result in better chemical stability. A concentration of 30 to 100% v/v of ethanol in the mixture is preferred.

In another embodiment, the stability of a CCI-779 or a proline-CCI-779 in parenterally acceptable alcoholic cosolvents is enhanced by addition of an antioxidant to the formulation. Acceptable antioxidants include, but are not limited to, citric acid, d,l-α-tocopherol, BHA, BHT, monothioglycerol, ascorbic acid, propyl gallate, and mixtures thereof. Generally, the parenteral formulations useful in this embodiment of the invention will contain an antioxidant component(s) in a concentration ranging from 0.001% to 1% w/v, or 0.01% to 0.5% w/v, of the cosolvent concentrate, although lower or higher concentrations may be desired. In one embodiment, d,l-α-tocopherol is used at a concentration of 0.01 to 0.1% w/v, or 0.075% w/v, of the cosolvent concentrate.

In other embodiments, the antioxidant component of the formulation of the invention also exhibits chelating activity. Examples of such chelating agents include, e.g., citric acid, acetic acid, and ascorbic acid (which may function as both a classic antioxidant and a chelating agent in the present formulations). Other chelating agents include such materials as are capable of binding metal ions in solution, such as ethylene diamine tetra acetic acid (EDTA), its salts, or amino acids such as glycine that are capable of enhancing the stability of a CCI-779 or a proline-CCI-779. In still other embodiments, components with chelating activity are included in the formulations of the invention as the sole "antioxidant component". In one embodiment, such metal-binding components, when acting as chelating agents, are used in the lower end of the range of concentrations for the antioxidant component provided herein. Additionally, such chelating agents may be used in combination with other antioxidants as part of the antioxidant component of the invention. For example, an acceptable formulation may contain both citric acid and d,l-α-tocopherol. Optimal concentrations for the selected antioxidant(s) can be readily determined by one of skill in the art, based upon the information provided herein.

Advantageously, in certain embodiments of the parenteral formulations useful in the invention, precipitation of a CCI-779 or a proline-CCI-779 upon dilution with aqueous infusion solutions or blood is prevented through the use of a surfactant contained in the diluent solution. The most important component of the diluent is a parenterally acceptable surfactant. One particularly desirable surfactant is polysorbate 20 or polysorbate 80. However, one of skill in the art may readily select other suitable surfactants from among salts of bile acids (taurocholate, glycocholate, cholate, deoxycholate, etc.) which are optionally combined with lecithin. Alternatively, ethoxylated vegetable oils, such as a pegylated castor oil [e.g., such as PEG-35 castor oil which is sold, e.g., under the name Cremophor EL, BASF], vitamin E tocopherol propylene glycol succinate (Vitamin E TGPS), and polyoxyethylene-polyoxypropylene block copolymers can be used in the diluent as a surfactant, as well as other members of the polysorbate family such as polysorbate 20 or 60 Other components of the diluent may include water, ethanol, polyethylene glycol 300, polyethylene 400, polyethylene 600, polyethylene 1000, or blends containing one or more of these polyethylene glycols, propylene glycol and other parenterally acceptable cosolvents or agents to adjust solution osmolarity such as sodium chloride, lactose, mannitol or other parenterally acceptable sugars, polyols and electrolytes. It is expected that the surfactant will comprise 2 to 100% w/v of the diluent solution, 5 to 80% w/v, 10 to 75% w/v, 15 to 60% w/v, or at least 5% w/v, or at least 10% w/v, of the diluent solution.

A parenteral formulation useful in the invention can be prepared as a single solution. In another embodiment, parenteral formulation useful in the invention can be prepared as a cosolvent concentrate containing a CCI-779 or a proline-CCI-779, an alcoholic solvent, and an antioxidant, which is subsequently combined with a diluent that contains a diluent solvent and suitable surfactant. Prior to use, the cosolvent concentrate is mixed with a diluent comprising a diluent solvent, and a surfactant. When a CCI-779 or a proline CCI-779 is prepared as a cosolvent concentrate according to this invention, the concentrate can contain concentrations of a CCI-779 or a proline-CCI-779 from 0.05 mg/mL, from 2.5 mg/mL, from 5 mg/mL, from 10 mg/mL or from 25 mg/mL up to approximately 50 mg/ml. The concentrate can be mixed with the diluent up to approximately 1 part concentrate to 1 part diluent, to give parenteral formulations having concentrations of a CCI-779 or a proline CCI-779 from 1 mg/mL, from 5 mg/mL, from 10 mg/mL, from 20 mg/mL, up to approximately 25 mg/ml. For example, the concentration of a CCI-779 or a proline-CCI-779 in the parenteral formulation may be from about 2.5 to 1 mg/mL. This invention also covers the use of formulations having lesser concentrations of a CCI-779 or a proline-CCI-779 in the cosolvent concentrate, and formulations in which one part of the concentrate is mixed with greater than 1 part of the diluent, e.g., concentrate:diluent in a ratio of about 1:1.5, 1:2, 1:3, 1:4, 1:5, or 1:9 v/v and so on, to parenteral formulations having a CCI-779 or a proline-CCI-779 concentration down to the lowest levels of detection.

In one embodiment, the antioxidant may comprise from about 0.0005 to 0.5% w/v of the formulation, the surfactant may comprise from about 0.5% to about 10% w/v of the formulation, and the alcoholic solvent may comprise from about 10% to about 90% w/v of the formulation.

The parenteral formulations useful in this invention can be used to produce a dosage form that is suitable for administration by either direct injection or by addition to sterile infusion fluids for intravenous infusion.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The present invention further provides packaging and kits containing the proline-CCI-779 or CCI-779 produced according to the present invention and formulated for administration by a suitable delivery method. A variety of suitable containers, including bottles, vials, blister packs, and the like are known to those of skill in the art. Such packaging and kits may further contain other components, including, e.g., instructions for use, syringes, applicators, and the like.

EXAMPLES

The following examples illustrate the production of proline CCI-779. It will be readily understood from the foregoing detailed description that the invention is not limited to the reagents and conditions provided in these examples.

Example 1—Synthesis of Proline CCI-779
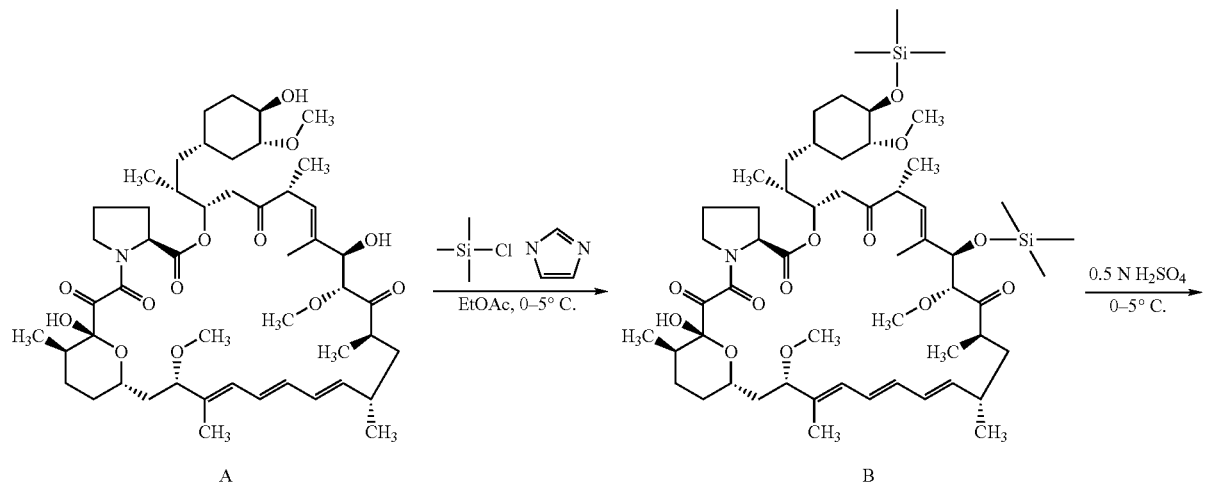
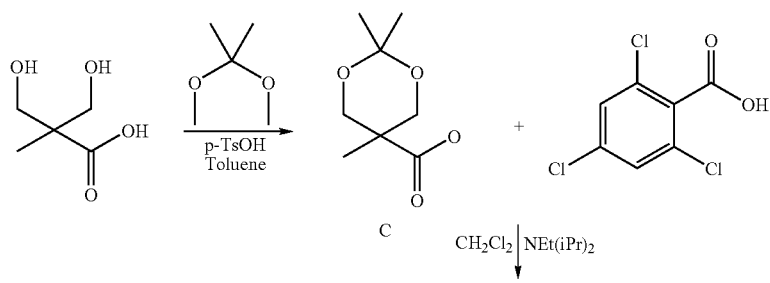
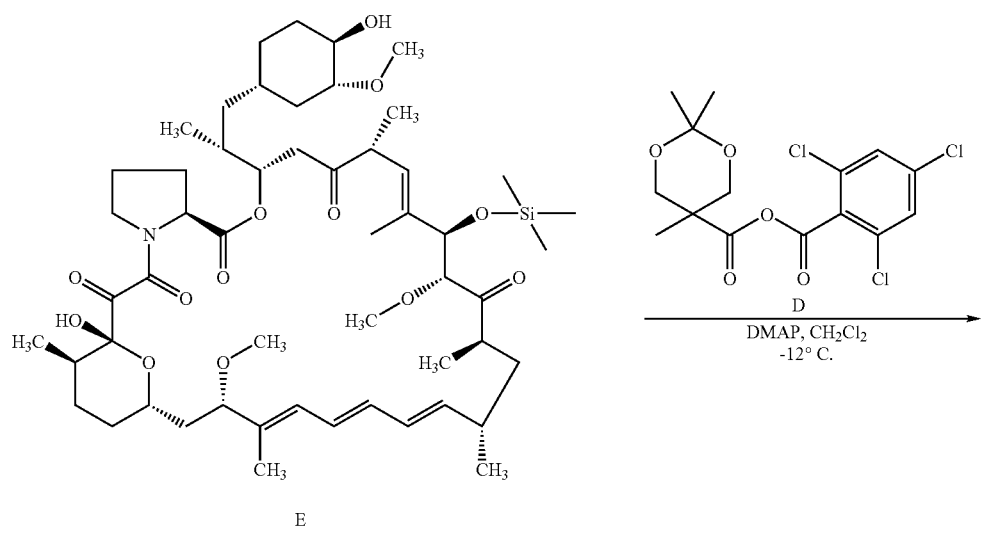

-continued
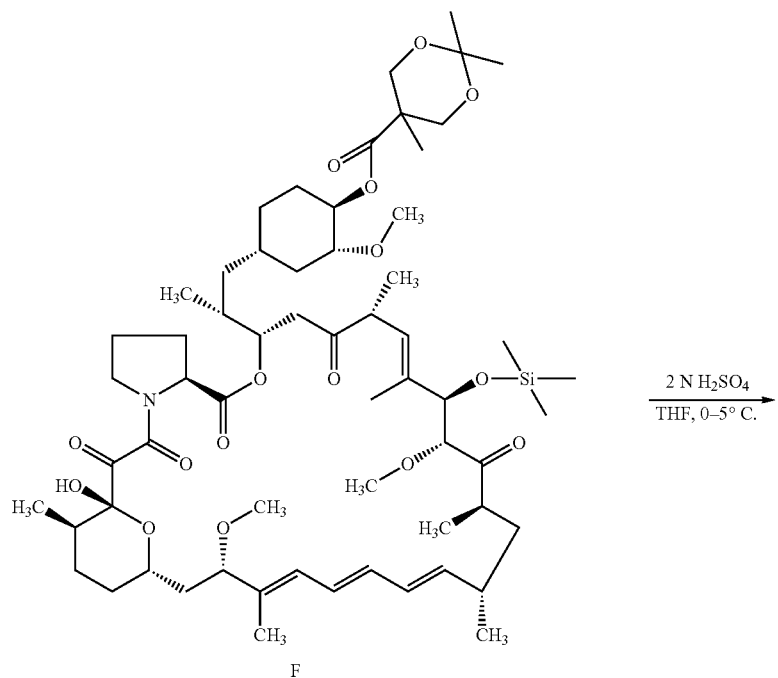
$\xrightarrow{\text{2 N H}_2\text{SO}_4}{\text{THF, 0–5° C.}}$
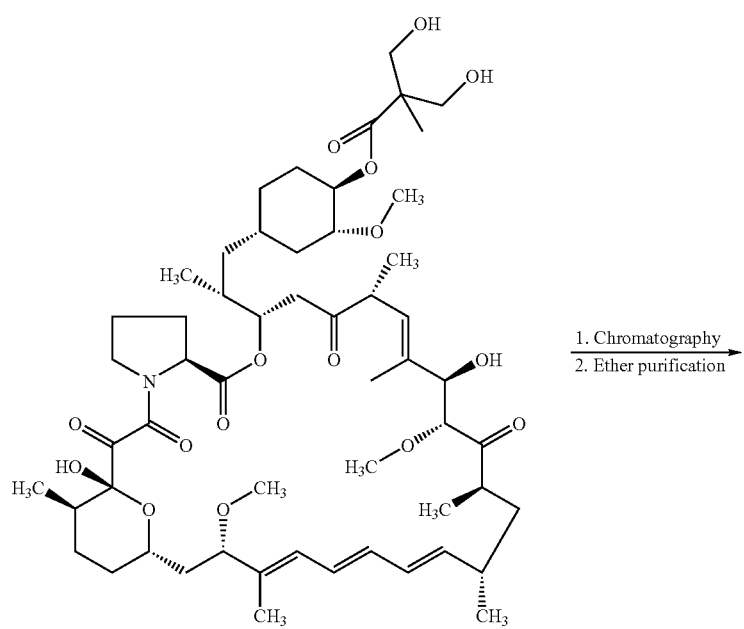
$\xrightarrow{\text{1. Chromatography}}{\text{2. Ether purification}}$

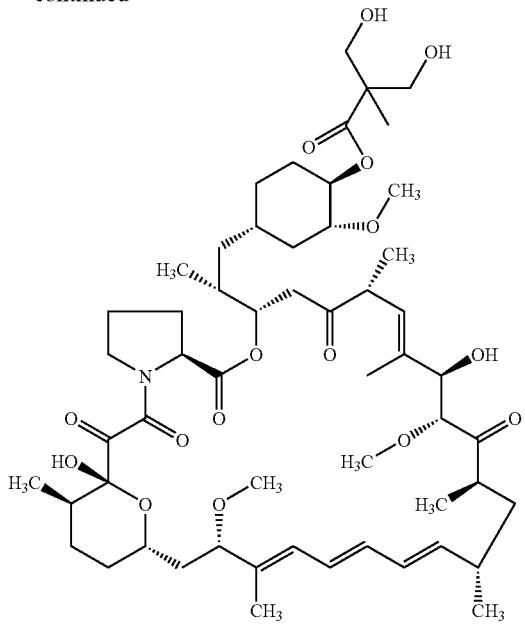

Proline-CCI-779

This example describes a method for the synthesis of the proline analog of CCI-779, which is illustrated in the scheme provided above.

A. Preparation of 31,42-Bis(trimethylsilyl)proline rapamycin (Compound B)

A 3-neck 50 mL flask was charged with proline rapamycin (compound A in the scheme) (1.47 g, 1.63 mmol), imidazole (0.45 g, 6.6 mmol, 4 eq.) and ethyl acetate (22.5 mL). The magnetically stirred mixture became cloudy. The mixture was cooled to 0–5° C. Under nitrogen protection, trimethylsilyl chloride (0.62 g, 5.7 mmol, 3.5 eq.) was added over 0.5 h via syringe while maintaining the temperature at 0–5° C. during the addition. The syringe was rinsed with 2.5 ml ethyl acetate and the mixture held for 0.75 hours (0.75 h), whereupon a white precipitate was formed. The reaction was monitored by thin layer chromatography (TLC) (30:70 acetone:heptane eluent). The TLC sample was prepared by quenching 3–4 drops of reaction mixture into 0.25 mL saturated sodium bicarbonate and 10 drops ethyl acetate. The mixture was shaken and allowed to settle. The upper organic layer was spotted against the starting material (proline rapamycin). The reaction was complete when no more starting material was present.

B. Preparation of 31-trimethylsilylproline rapamycin, Compound E

When the above reaction was complete, 2–3 drops of the reaction mixture was removed and retained for the following step as the 31,42-bis(trimethylsilyl) proline rapamycin reference standard. To the 50 ml flask was added 0.5 N sulfuric acid (4.5 mL) over 0.5 h maintaining the temperature at 0–5° C. The mixture became less cloudy. The mixture was held for 2.5 h and was monitored by thin layer chromatography (TLC, 30:70 acetone:heptane eluent). The TLC sample was prepared by quenching 3–4 drops of reaction mixture into 0.25 mL saturated sodium bicarbonate and 10 drops ethyl acetate. The reaction aliquot was shaken and allowed to settle. The upper organic layer was spotted against the 31,42-bis(trimethylsilyl) proline rapamycin reference. The reaction was complete when essentially no 31,42-bis(trimethylsilyl) proline rapamycin was present. Ethyl acetate (5 mL) was added and the layers separated. The lower aqueous layer is extracted with ethyl acetate (7.5 mL). The combined organic layers were washed with brine (7.5 mL), by washing with saturated sodium bicarbonate (6 mL) followed by washing water (3×7.5 mL), in that order. The pH of the last water wash was 6–7. The organic layer was washed again with brine (7.5 mL) and dried over sodium sulfate (4 g) for 20 min. The mixture was filtered into a 250 mL flask and concentrated to dryness. The solid was dried at room temperature under high vacuum (10 mmHg or less) for 20 h. Weight=1.51 g of an off-white foam.

C. Preparation of Intermediate, Compound F:

A 3-neck 100 mL flask equipped with mechanical stirrer was charged with 2,2,5-trimethyl[1,3-dioxane]-5-carboxylic acid, Compound C (0.63 g, 3.6 mmol) in methylene chloride (7.5 mL). Diisopropylethylamine (0.77 g, 5.9 mmol) was added, followed by a rinse with methylene chloride (1 mL). 2,4,6-Trichlorobenzoyl chloride (0.85 g, 3.5 mmol) was added, followed by a rinse with methylene chloride (1.5 mL). The mixture was held at room temperature for 4.5 h. The solution was cooled to −12±2° C.

31-Trimethylsilyl proline rapamycin, compound E, (1.51 g) in methylene chloride (8 mL) was dissolved and added to the 100 mL flask. Methylene chloride (2 mL) was added as a rinse. A solution of dimethylamino pyridine (DMAP) (0.77 g, 6.8 mmol) in methylene chloride (3 mL) was prepared and added to the 100 mL flask over 2.5 h maintaining the temperature −12±2° C. Methylene chloride (1 mL) was added as a rinse. The mixture was held for 16 h and was monitored by HPLC by quenching 3–4 drops of reaction mixture into 0.25 mL water and 0.2 mL ethyl acetate. The HPLC sample was prepared by withdrawing 2 drops of the upper organic layer, blowdrying the sample under nitrogen in an HPLC vial and redissolving using the mobile phase.

| HPLC column: | CSC Hypersil ODS/BDS 5 μm. | |
|---|---|---|
| Mobile phase: | 68.5% dioxane:water + 0.01M $KH_2PO_4$ | |
| Wavelength: | $\lambda$ = 280 nm | |
| Flow rate: | 1 mL/min | |
| Time: | 60 min | |
| Retention times: | Compound E | ~14.0–14.5 min |
| | Compound F | ~33.4–33.8 min |

The reaction was complete when <0.5% of starting material was present. The reaction mixture was quenched with water (6 mL). Methylene chloride (10 mL) was added and the layers separated. The aqueous layer was extracted with methylene chloride (10 mL). The combined organic layers were washed with 0.5 N sulfuric acid (12 mL), brine (10 mL), saturated sodium bicarbonate (6 mL), and water (3×10 mL) in that order. The pH of the last water wash was 6–7. The clear yellow solution was concentrated to a foam. The solid was dried at room temperature under high vacuum (10 mmHg or less) for 24 h. Weight=1.88 g of a yellow foam.

D. Preparation of Crude Proline CCI-779

A 1-neck 50 mL flask equipped with mechanical stirrer was charged with Compound F in THF (18.8 mL, 10 vols) and then cooled to 0–5° C. (or about –2.5° C.). 2 N sulfuric acid (9.4 mL, 5 vols) was added over 2.5 h. After complete addition, the mixture was warmed to 2.5° C. and then held for 45 h. The reaction was monitored by HPLC by quenching 3–4 drops of reaction mixture into 0.25 mL saturated sodium bicarbonate and 0.25 mL ethyl acetate. The HPLC sample was prepared by withdrawing 5 drops of the upper organic layer, blow drying the sample under nitrogen in an HPLC vial and redissolving using the mobile phase.

| HPLC column: | CSC Hypersil ODS/BDS 5 μm. | |
|---|---|---|
| Mobile phase: | 68.5% dioxane:water + 0.01M $KH_2PO_4$ | |
| Wavelength: | $\lambda$ = 280 nm | |
| Flow rate: | 1 mL/min | |
| Time: | 60 min | |
| Retention times: | Compound F | ~33.4–33.8 min |
| | Desilylated Compound F (intermediate) | ~10.5–11.5 min |
| | Proline CCI-779 | ~5.0–5.5 min |

The desilylated intermediate of compound F was formed first. The reaction was complete when <0.5% of the silylated analog remained. Ethyl acetate (27 mL) and brine (7.5 mL) was added and the layers separated. The aqueous layer was extracted with ethyl acetate (10 mL). The combined organic layers were washed with brine (10 mL), saturated sodium bicarbonate (7.5 mL), and water (3×7.5 mL) in that order. The pH of the last water wash was 6–7. The mixture was dried over sodium sulfate (5 g) for 30 min, filtered into a 250 mL flask and concentrated to dryness. Weight=1.58 g of a yellow foam.

E. Chromatographic purification of crude proline CCI-779

A silica gel column (31.6 g, 60 Å, 200–400 mesh) (22 cm length×2.5 cm diameter) was prepared and conditioned with 15:85 acetone:HPLC grade hexane (1 L). The yellow crude proline CCI-779 (1.58 g) in acetone (1.58 mL) was prepared and chromatographed. The column was eluted with the remaining 15:85 acetone:hexane mixture followed by 25:75 acetone:hexane (4 L). The positive fractions were combined and concentrated to dryness. The resulting foam was dried at 35° C., high vacuum (i.e., 10 mmHg or less) for 24 h. Weight=1.12 g of a light yellow foam.

F. Ether treatment of proline CCI-779

A 1-neck 50 mL flask was charged with proline CCI-779 (1.12 g) and dissolved in ether (1.5 mL). The mixture was held for 2 h. The ether was stripped to give a foam. The foam was dried at 35° C., under high vacuum (10 mmHg or less) for 12 h then at room temperature overnight (12 h). Weight=1.09 g. $^1$H NMR (500 and 600 MHz, DMSO-$d_6$) δ 5.45 (H-1), 6.12 (H-2), 6.27 (H-3), 6.41 (H-4), 6.20 (H-5), 3.66 (H-7), 1.14 and 1.86 (H-8), 4.02 (H-9), 1.19 and 1.81 (H-10), 1.52 (H-11), 2.03 (H-12), 3.23 and 3.54 (H-18), 1.76 (H-19), 2.20 and 1.89 (H-21), 4.22 (H-22), 4.87 (H-25), 2.28 and 2.70 (H-26), 3.22 (H-28), 5.11 (H-29), 4.04 (H-31), 4.17 (H-32), 2.25 (H-34), 0.985 and 1.38 (H-35), 2.22 (H-36), 1.76 (H-37), 0.961 and 1.11 (H-38), 1.31 (H-39), 0.726 and 1.90 (H-40), 3.14 (H-41), 4.46 (H-42), 1.22 and 1.81 (H-43), 0.888 and 1.60 (H-44), 1.60 (H-45), 3.05 (H-46, $OCH_3$), 0.697 (H-47), 6.48 (H-48), 0.821 (H-49), 1.76 (H-50), approx. 5.1–5.3 (H-51), 3.17 (H-52, $OCH_3$), 0.755 (H-53), 0.966 (H-54), 0.805 (H-55), 3.29 (H-56, $OCH_3$), 3.46 (H-59), 1.01 (H-60), approx. 4.3–4.7 (0-61). $^{13}$C NMR (75 MHz, DMSO-$d_6$) δ 139.12 (C-1), 130.53 (C-2), 132.49 (C-3), 127.08 (C-4), 127.21 (C-5), 137.12 (C-6), 81.93 (C-7), 40.40 (C-8), 65.83 (C-9), 29.45 (C-10), 25.87 (C-11), 34.21 (C-12), 99.25 (C-13), 198.17 (C-15), 165.55 (C-16), 47.01 (C-18), 24.04 (C-19), 28.93 (C-21), 58.50 (C-22), 170.44 (C-23), 73.24 (C-25), 39.96 (C-26), 207.67 (C-27), 44.51 (C-28), 123.92 (C-29), 136.56 (C-30), 75.84 (C-31), 84.86 (C-32), 209.49 (C-33), 40.76 (C-34), 39.20 (C-35), 35.05 (C-36), 32.73 (C-37), 38.42 (C-38), 32.06 (C-39), 36.01 (C-40), 80.12 (C-41), 75.92 (C-42), 29.25 (C-43), 30.24 (C-44), 10.27 (C-45), 55.48 (C-46, $OCH_3$), 15.46 (C-47), 15.59 (C-49), 14.41 (C-50), 56.56 (C-52, $OCH_3$), 12.67 (C-53), 21.50 (C-54), 14.89 (C-55), 57.27 (C-56, $OCH_3$), 174.22 (C-57), 49.90 (C-58), 63.59 and 63.98 (C-59), 16.82 (C-60). MS [M+$NH_4^+$] 1033.5, [ESI(+), M+$Na^+$] 1038.7.

The following examples illustrate the regiospecific production of CCI-779. Example 2 illustrates production of vinyl esters useful in the invention. However, the invention is not limited to these vinyl esters or these methods of production. Suitable alternative methods for generating vinyl esters are well known to those of skill in the art. Example 3 illustrates the regiospecific production of CCI-779 using the vinyl esters of Example 2, and Example 4 illustrates the regiospecific production of proline-CCI-779 using the vinyl esters of Example 2. It will be readily understood from the foregoing detailed description that the invention is not limited to the reagents and conditions provided in these examples.

Example 2—Synthesis of Vinyl Ester

A. Synthesis of I:

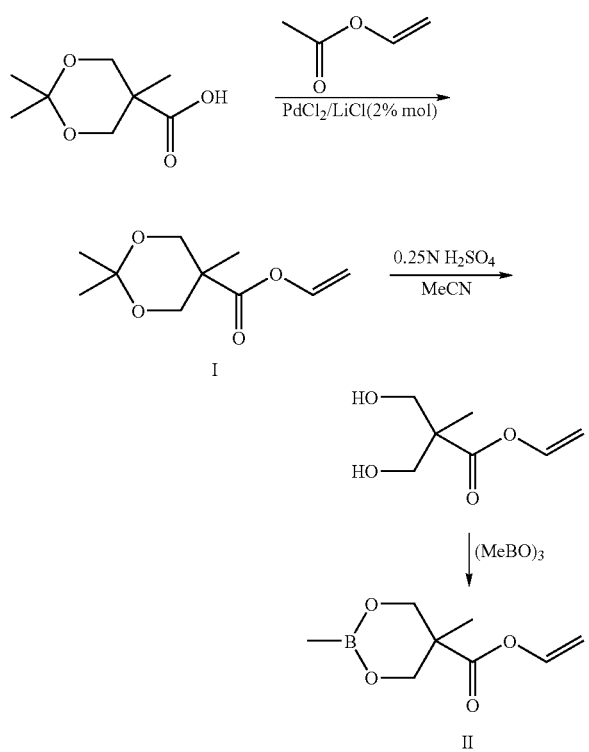

PdCl$_2$ (708 mg, 4 mmol), LiCl (168 mg, 4 mmol) in MeOH (16 mL) was heated under reflux until the mixture become a clear solution, MeOH was then removed under reduced pressure, vinyl acetate (10 mL) was added and the solution was concentrated to dryness. The residue was then re-dissolved in vinyl acetate (20 mL) and was added to a mixture of 2,2-bis(hydroxymethyl)propionic acid (34.8 g, 200 mmol) in vinyl acetate (280 mL). The mixture was then gently refluxed overnight (about 16 h). The solution was concentration under reduced pressure, to this residue heptane (150 mL) was added and the black precipitation was removed by filtration through a pad of celite. The heptane solution was concentrated and the residue was distilled under reduced pressure to give vinyl ester I as a colorless liquid (30.1 g, 75%)

B. Synthesis of II:

A solution of I (10 g) in MeCN (50 mL) was treated with aqueous H$_2$SO$_4$ (20 mL, 0.25 N) for 4 h at room temperature. The mixture was then diluted with EtOAc, washed with brine, 2.5% NaHCO$_3$, and brine. The organic layers were dried over MgSO$_4$. Filtration and concentration to about 60 mL, then (MeBO)$_3$ (2.2 mL) was added dropwise to above solution. The mixture was stirred at room temperature for 1.5 h, diluted with hexane (60 mL), MgSO$_4$ (3 g) was added and the mixture was stirred for another 10 min. Filtration and concentration afford an oily residue which was distilled under reduced pressure to give II as a colorless liquid (7.2 g, 78%)

Example 3—Synthesis of CCI-779

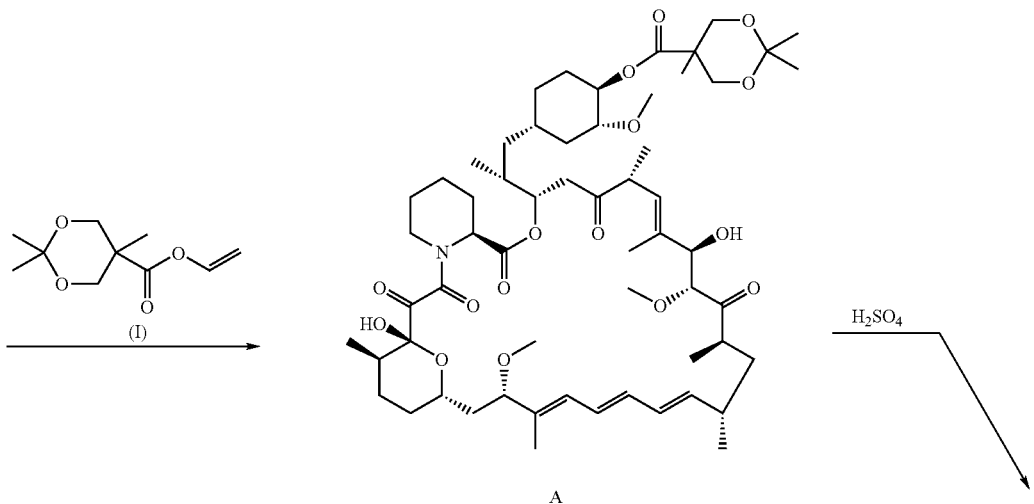

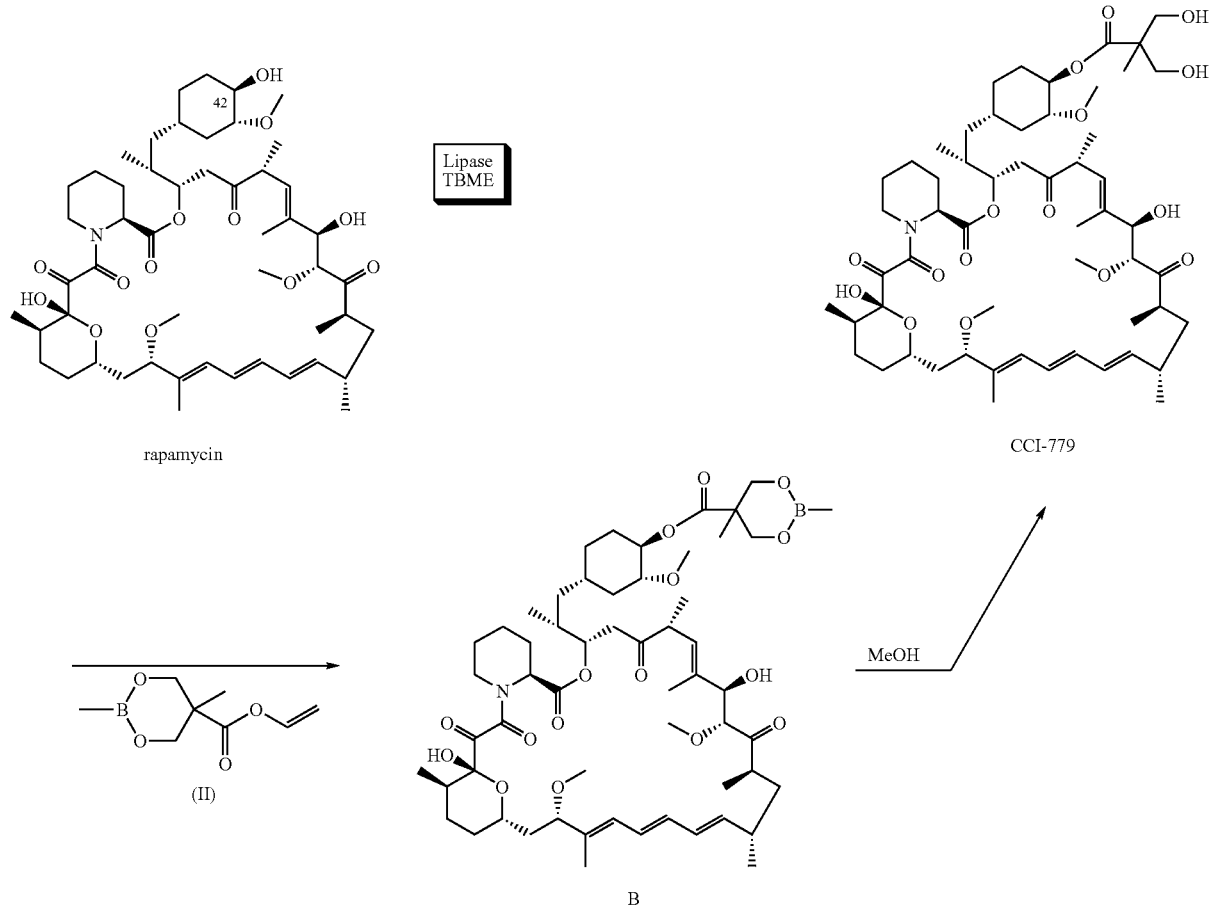

A. Synthesis of CCI-779 via intermediate A
Method 1:

A mixture of rapamycin (6 g), vinyl ester I (2 g), lipase PS-C "Amano" II (6 g) in anhydrous TBME (36 mL) was heated at 45° C. under $Ar_2$ for 2 days. The mixture was cooled to room temperature and enzyme was removed by filtration, the filtrate was concentrated, the oily residue was added to heptane while stirring. The batch was then cooled to −15° C. for 2 h, collect the solid on the Buchner funnel and washed with cold heptane, A was obtained as off-white solid, crude yield: 98%.MS (EI): 1070

Above crude A (6 g), dissolved in n-PrOH (24 mL) cooled to 0° C. with an ice-water bath, to this solution was added aqueous $H_2SO_4$ (12 mL, 1.2N). The mixture was stirred for 24 h at 0° C. and was then added to cold phosphate buffer (300 ml, pH=7.8), collect the solid on a Buchner funnel and washed with DI water and dry under vacuum, silica gel column purification eluting with hexane-acetone furnished CCI-779 as a white solid (5.2 g, 90%). MS (EI): 1030

Method 2:

A mixture of rapamycin (30.0 g, 32.8 mmol), vinyl ester I (10.0 g, 50 mmol), lipase PS-C "Amano" II (30 g) and molecular sieves (5Å) (10.0 g) in anhydrous TBME (150 mL) was heated at 42–43° C. under $Ar_2$ for 48 hours. THF (100 mL) was added to dissolve the precipitation and the mixture was cooled to room temperature. Enzyme was removed by filtration and washed with THF (200 mL), the filtrate was concentrated to about 60 mL and diluted with THF (320 mL). The solution was then cooled to 0–5° C., $H_2SO_4$ (180 mL, 2N) was added dropwise over 1 h. The mixture was stirred for 48 h at 0–5° C. or until the disappearance of A as monitored by TLC. The mixture was diluted with brine (300 mL) and extracted with EtOAc (three times). The combined organic layer was washed with $H_2O$, 5% $NaHCO_3$, then brine and dried ($MgSO_4$). Evaporation of solvent gave a light yellowish semi solid which was purified by flash chromatography (hexane/acetone, 2:1) to give CCI-779 as a white solid (30.77 g, 91% for two steps).

B. Synthesis of CCI-779 via intermediate B:

A mixture of rapamycin (3 g), vinyl ester II (1.2 g), lipase PS-C "Amano" II (5 g) in anhydrous TBME (45 mL) was heated at 45° C. under $Ar_2$ for 60 h. The mixture was cooled to room temperature and enzyme was removed by filtration, the filtrate was concentrated, MeOH (20 mL) was added to the residue and concentrated to dryness. Silica gel column purification of crude eluting with hexane-acetone furnished CCI-779 as a white solid (2.3 g), and recovered rapamycin (0.81 g). The yield is 93% based on the recovered rapamycin.

Example 4—Synthesis of Proline-CCI-779

The enzymatic procedure of the invention can also be applied to the synthesis of proline CCI-779 from proline-rapamycin under essentially the same conditions as described in Example 2, procedure A for the synthesis of CCI-779 from rapamycin.
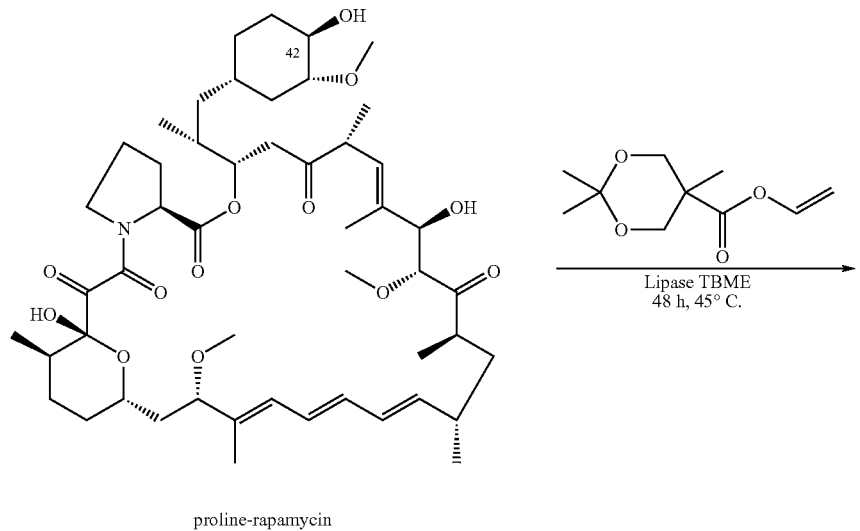
proline-rapamycin
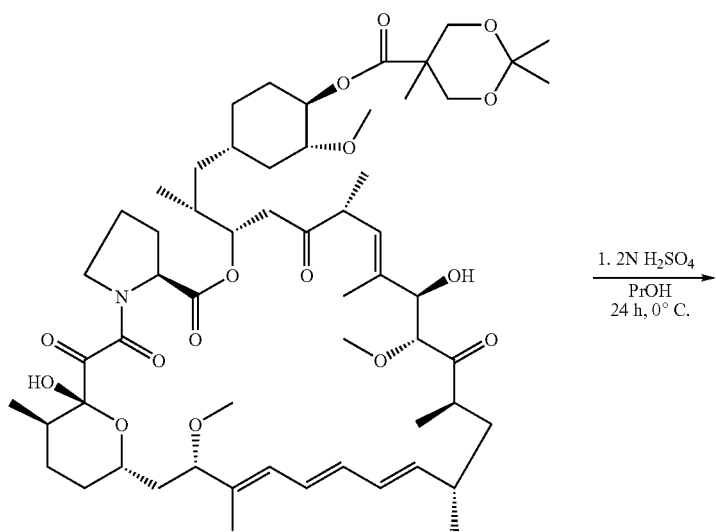

-continued

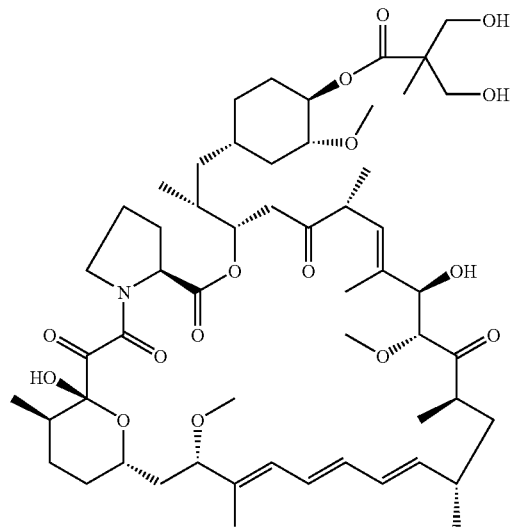

proline-CCI-779

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Patents, patent applications, publications, procedures, and the like are listed throughout this application, the disclosures of which are incorporated herein by reference in their entireties. To the extent that a conflict may exist between the specification and a reference, the language of the disclosure made herein controls.

The invention claimed is:

1. Proline-rapamycin 42-ester with 2,2-bis(hydroxymethyl)propionic acid (proline-CCI-779).

2. A method for the regiospecific preparation of a rapamycin 42-ester or proline-rapamycin 42-ester with 2,2-bis(hydroxymethyl)propionic acid (CCI-779 and proline-CCI-779) comprising the steps of:
 (a) reacting rapamycin or proline-rapamycin with an activated ester having the structure

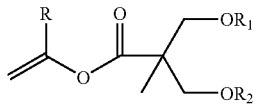

wherein R is hydrogen or methyl, $R_1$ and $R_2$ are hydrogen, or taken together to form a ketal with the structure

wherein $R_3$ and $R_4$ are each, independently, hydrogen, $C_{1-6}$ alkyl, either linear or branched, or taken together form $C_{5-7}$ cycloalkyl or taken together form cyclic boronate with the structure,

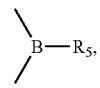

wherein $R_5$ is selected from methyl, ethyl, n-propyl, iso-propyl, n-butyl, iso-butyl and phenyl;
 in a suitable organic solvent in the presence of an effective amount of microbial lipase; and
 (b) deprotecting the intermediate resulting from step (a) to provide CCI-779 or proline-CCI-779.

3. The method according to claim 2, wherein the activated ester is a vinyl ester.

4. The method according to claim 3 wherein the activated ester is selected from the group consisting of vinyl ester (I) and vinyl ester (II).

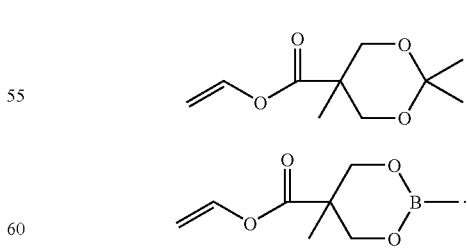

5. The method according to claim 2, wherein the microbial lipase used is a lipase from microorganisms *Aspergillus niger, Candida antarctica, Candida rugosa, Mucor niiehei, Pseudomonas cepacia, Pseudomonas fluorescens, Rhizopus delemar.*

6. The method according to claim 5, wherein the lipase used is lipase PS or PS-C from *Pseudomonas cepacia.*

7. The method according to claim 2, wherein the suitable organic solvent is selected from the group consisting of toluene, tert-butyl methyl ether (TBME), ethyl ether, THF (tetrahydrofuran), MeCN, $CH_2Cl_2$, $CHCl_3$, $^iPr_2O$, hexane, dioxane, or mixtures including these solvents.

8. The method according to claim 2, further comprising adding a drying agent in step (a) selected from the group consisting of anhydrous $MgSO_4$ and anhydrous $Na_2SO_4$.

9. The method according to claim 2, further comprising applying a molecular sieve to the reaction in step (a).

10. The method according to claim 2, wherein the reaction in step (a) is conducted at a temperature of 20° C. to 75° C.

11. The method according to claim 2, wherein deprotecting step (b) comprises dissolving boronate-protected CCI-779 or boronate-protected proline-CCI-779 in an alcoholic solvent selected from the group consisting of methanol, ethanol, propanol, isopropanol, butanol, iso-butanol, ethylene glycol, 1,3-propanediol, and 2-methylpentane-2,5-diol, or a mixture thereof.

12. The method according to claim 2, wherein deprotecting step (b) for ketal-protected CCI-779 or ketal-protected proline-CCI-779 is performed in cold diluted acid in the presence of a water-miscible organic solvent.

13. A method for the preparation of a proline-rapamycin 42-ester with 2,2-bis(hydroxymethyl)propionic acid (proline-CCI-779) comprising the steps of:

bis-silylating proline rapamycin using trimethylsilyl chloride and imidazole in ethyl acetate to form 31,42-bis-trimethylsilyl proline;

mono-de-protecting 31,42-bis-trimethylsilyl proline rapamycin at the 42-position under dilute acid conditions to provide 31-trimethylsilyl proline rapamycin;

reacting a mixed anhydride with 31-trimethylsilyl proline rapamycin and dimethylaminopyridine in methylene chloride; and hydrolyzing the product to provide proline-CCI-779.

14. A pharmaceutical composition comprising a proline-rapamycin 42-ester with 2,2-bis(hydroxymethyl)propionic acid (proline-CCI-779) according to claim 1 and a physiologically compatible carrier.

* * * * *